(12) United States Patent
Linker et al.

(10) Patent No.: US 6,172,225 B1
(45) Date of Patent: Jan. 9, 2001

(54) PROCESS FOR PRODUCING HYDROXYARENES

(75) Inventors: Karl-Heinz Linker, Leverkusen; Wilhelm Haas, Pulheim; Otto Schallner, Monheim; Kurt Findeisen, Leverkusen; Roland Andree; Mark Wilhelm Drewes, both of Langenfeld, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/180,777

(22) PCT Filed: May 12, 1997

(86) PCT No.: PCT/EP97/02410

§ 371 Date: Nov. 12, 1998

§ 102(e) Date: Nov. 12, 1998

(87) PCT Pub. No.: WO97/45398

PCT Pub. Date: Dec. 4, 1997

(30) Foreign Application Priority Data

May 24, 1996 (DE) ............................... 196 20 992

(51) Int. Cl.$^7$ ............... C07D 239/02; C07D 249/12; C07D 231/04; C07C 255/00
(52) U.S. Cl. ............... 544/309; 548/263.2; 548/377.1; 548/366.1; 558/425
(58) Field of Search ............... 548/263.2, 377.1, 548/366.1; 558/425; 544/309

(56) References Cited

U.S. PATENT DOCUMENTS

| | | |
|---|---|---|
| 5,069,711 | 12/1991 | Fischer et al. ............ 504/283 |
| 5,221,318 | 6/1993 | Fischer et al. ............ 504/283 |
| 5,464,810 | 11/1995 | Haas et al. ............... 504/273 |
| 5,593,945 | 1/1997 | Andree et al. ............. 54/243 |
| 5,663,362 | 9/1997 | Haas et al. ............... 548/263.2 |
| 5,681,794 | 10/1997 | Andree et al. ............. 504/243 |
| 5,756,805 | 5/1998 | Schallner et al. .......... 558/413 |

OTHER PUBLICATIONS

Bull. Korean Chem. Soc., vol. 14, (Month unavailable) 1993, p. 717.

Primary Examiner—Joseph McKane
Assistant Examiner—Joseph Murray

(74) Attorney, Agent, or Firm—Joseph C. Gil; Carol Marmo

(57) ABSTRACT

The invention relates to a novel process for producing thereof hydroxyarenes of the general formula (I)

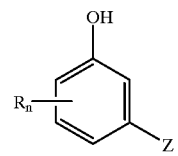

(I)

in which n represents the numbers 1, 2, 3 or 4,

R represents cyano, carboxyl, formyl, nitro, halogen or represents alkyl, alkoxy, alkylthio, alkylsulphinyl, alkylsulphonyl, alkylcarbonyl or alkoxycarbonyl, each of which is optionally substituted, and Z represents hydrogen, cyano, nitro, halogen, alkyl, halogenoalkyl, or represents monocyclic or bicyclic, saturated or unsaturated heterocyclyl, heterocyclylamino or heterocyclylimino, each of which is optionally substituted, characterized in that halogenoarenes of the general formula (II)

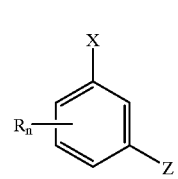

(II)

in which n, R and Z are each as defined above and

X represents halogen are reacted with 3-hydroxy-propionitrile of the formula (III),

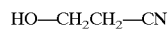

HO—CH$_2$CH$_2$—CN (III), if appropriate in the presence of a reaction auxiliary and if appropriate in the presence of a diluent, at temperatures between 0° C. and 100° C.

8 Claims, No Drawings

PROCESS FOR PRODUCING HYDROXYARENES

This Application is a 371 of PCT/EP97/02410 filed May 12, 1997.

TECHNICAL FIELD OF THE INVENTION

The invention relates to a novel process for producing thereof hydroxyarenes which can be used as active compounds or as intermediates for preparing active compounds, in particular herbicides.

BACKGROUND OF THE INVENTION

Methods for the preparation of hydroxyarenes ("phenols") have been known for a long time and are part of the "textbook knowledge" of organic chemistry. Hydroxyarenes are generally prepared by reaction of metal hydroxides with arenes containing groups which are easily nucleophilically substitutable. With this approach, problems may occur if the starting materials contain other groups which are easily attacked by a nucleophilic mechanism, such as, for example, cyano or ester groups. Undesirable side reactions are also observed in the alternatively possible synthesis by cleavage of appropriate methoxyarenes (cf. DE-A 38 35 168 and Bull. Korean Chem. Soc. 14 (1993), 717). It is an object of the present invention to provide a process which makes it possible to introduce hydroxy groups into arenes without affecting other groups which are easily attacked, such as, in particular, the cyano group.

DETAILED DESCRIPTION OF THE INVENTION

This invention, accordingly, provides hydroxyarenes of the general formula (I)

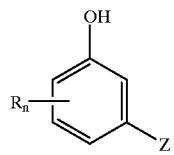
(I)

in which n represents the numbers 1, 2, 3 or 4,

R represents cyano, carboxyl, formyl, nitro, halogen or represents alkyl, alkoxy, alkylthio, alkylsulphinyl, alkylsulphonyl, alkylcarbonyl or alkoxycarbonyl, each of which is optionally substituted, and z represents hydrogen, cyano, nitro, halogen, alkyl, halogenoalklyl, or represents monocyclic or bicyclic, saturated or unsaturated heterocyclyl, heterocyclylamino or heterocyclylimino, each of which is optionally substituted, in high yields and in good quality by reaction of halogenoarenes of the general formula (II)

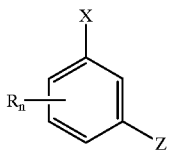
(II)

in which n, R and Z are each as defined above and

X represents halogen with 3-hydroxy-propionitrile of the formula (III)

HO—CH$_2$CH$_2$—CN          (III), if appropriate in the presence of a reaction auxiliary and if appropriate in the presence of a diluent, at temperatures between 0° C. and 100° C.

Surprisingly, it is possible using the process according to the invention to obtain hydroxyarenes of the general formula (I) in a simple and gentle manner in high yields and in good quality without affecting groups, such as, in particular, cyano groups, which are sensitive towards nucleophiles.

The process according to the invention therefore represents a useful addition to the prior art.

The process according to the invention preferably relates to the preparation of compounds of the formula (I) in which n represents the numbers 1, 2 or 3, R represents cyano, carboxyl, formyl, nitro, halogen or represents alkyl, alkoxy, alkylthio, alkylsulphinyl, alkylsulphonyl, alkylcarbonyl or alkoxycarbonyl having in each case 1 to 6 carbon atoms and being in each case optionally substituted by cyano, halogen, $C_1$–$C_4$-alkoxy or $C_1$–$C_4$-alkylthio, Z represents hydrogen, cyano, halogen or represents monocyclic or bicyclic, saturated or unsaturated heterocyclyl, heterocyclylamino or heterocyclylimino having in each case 2 to 6 carbon atoms and 1 to 4 nitrogen atoms in the heterocyclic ring system and being in each case optionally substituted, which optionally additionally contains an oxygen or sulphur atom and or optionally up to three groups selected from the series —CO—, —CS—, —SO— and/or SO$_2$—, and which is optionally substituted by one or more groups selected from the series nitro, hydroxyl, amino, cyano, carboxyl, carbamoyl, thiocarbamoyl, halogen, $C_1$–$C_6$-alkyl (which is optionally substituted by halogen or $C_1$–$C_4$-alkoxy), $C_2$–$C_6$-alkenyl or $C_2$–$C_6$-alkinyl (which are in each case optionally substituted by halogen), $C_1$–$C_6$-alkoxy or $C_1$–$C_6$-alkoxy-carbonyl (which are in each case optionally substituted by halogen or $C_1$–$C_6$-alkoxy), $C_2$–$C_6$-alkenyloxy or $C_2$–$C_6$-alkinyloxy (which are in each case optionally substituted by halogen), $C_1$–$C_6$-alkylthio, $C_2$–$C_6$-alkenylthio or $C_2$–$C_6$-alkinylthio (which are in each case optionally substituted by halogen), $C_1$–$C_6$-alkylamino or di-($C_1$–$C_4$-alkyl)-amino, $C_3$–$C_6$-cycloalkyl or $C_3$–$C_6$-cycloalkyl-$C_1$–$C_4$-alkyl (which are in each case optionally substituted by halogen and/or $C_1$–$C_4$-alkyl), phenyl, phenoxy, phenylthio, phenylsulphinyl, phenylsulphonyl or phenylamino (which are in each case optionally substituted by nitro, cyano, halogen, $C_1$–$C_4$-alkyl, $C_1$–$C_4$-halogenoalkyl, $C_1$–$C_4$-alkyloxy, $C_1$–$C_4$-halogenoalkyloxy and/or $C_1$–$C_4$-alkoxy-carbonyl).

The process according to the invention in particular relates to the preparation of compounds of the formula (I) in which n represents the numbers 1 or 2, R represents cyano, carboxyl, formyl, nitro, halogen or represents methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl or ethoxycarbonyl, each of which is optionally substituted by cyano, halogen, methoxy, ethoxy, methylthio or ethylthio, Z represents hydrogen, cyano, halogen or represents monocyclic or bicyclic, saturated or unsaturated heterocyclyl, heterocyclylamino or heterocyclylimino having in each case 2 to 6 carbon atoms and 1 to 4 nitrogen atoms in the heterocyclic ring system and being in each case optionally substituted, which optionally additionally contains an oxygen or sulphur atom and/or optionally up to two groups selected from the series —CO—, —CS—, —SO— and/or $SO_2$—, and which is optionally substituted by one or more groups selected from the series nitro, hydroxyl, amino, cyano, carboxyl, carbamoyl, thiocarbamoyl, fluorine, chlorine, bromine; methyl, ethyl, n- or i-propyl, n-, i-, s- or t-butyl (which are optionally substituted by fluorine, chlorine, methoxy or ethoxy); propenyl, butenyl, propinyl or butinyl (which are in each case optionally substituted by fluorine or chlorine); methoxy, ethoxy, n- or i-propoxy, n-, i-, s- or t-butoxy, methoxycarbonyl or ethoxycarbonyl (which are in each case optionally substituted by fluorine, chlorine, methoxy or ethoxy); propenyloxy, butenyloxy, propinyloxy or butinyloxy (which are optionally substituted by fluorine or chlorine); methylthio, ethylthio, n- or i-propylthio, n-, i-. s- or t-butylthio, propenylthio, butenylthio, propinylthio or butinylthio (which are in each case optionally substituted by fluorine or chlorine); methylamino, ethylamino, n- or i-propylamino, n-, i-. s- or t-butylamino, dimethylamino or diethylamino; cyclopropyl, cyclobutyl, cyclopentyl, cyclohexyl, cyclopropylmethyl, cyclobutylmethyl, cyclopentylmethyl or cyclohexylmethyl (which are in each case optionally substituted by fluorine, chlorine, methyl, ethyl n- or i-propyl), phenyl, phenoxy, phenylthio, phenylsulphinyl, phenylsulphonyl or phenylamino (which are in each case optionally substituted by nitro, cyano, fluorine, chlorine, bromine, methyl, ethyl, n- or i-propyl, trifluoromethyl, methoxy, ethoxy, n- or i-propoxy, difluoromethoxy, trifluoromethoxy, methoxycarbonyl or ethoxycarbonyl).

Z in the formulae (I) and (II) represents in particular the heterocyclic groups listed below:

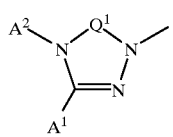
($Z^1$)

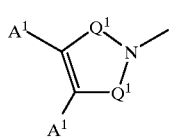
($Z^2$)

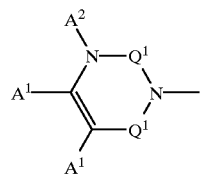
($Z^3$)

($Z^4$)

($Z^5$)

($Z^6$)

($Z^7$)

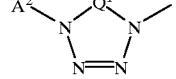
($Z^8$)

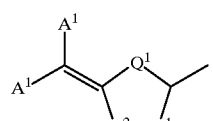
($Z^9$)

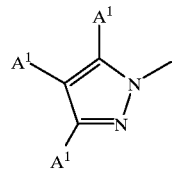
($Z^{10}$)

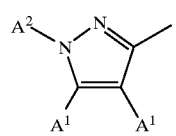
($Z^{11}$)

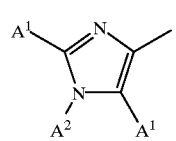
($Z^{12}$)

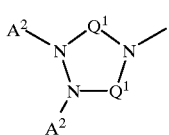 (Z¹³)

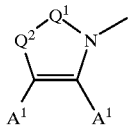 (Z¹⁴)

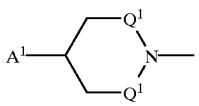 (Z¹⁵)

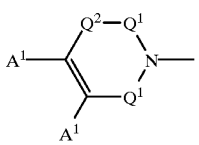 (Z¹⁶)

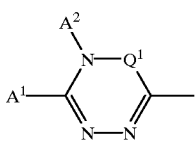 (Z¹⁷)

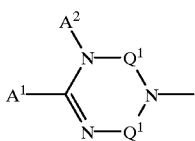 (Z¹⁸)

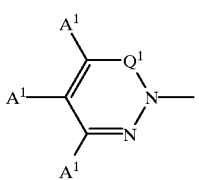 (Z¹⁹)

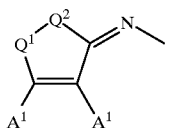 (Z²⁰)

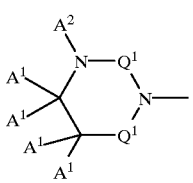 (Z²¹)

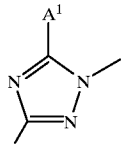 (Z²²)

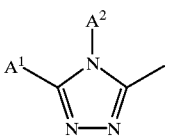 (Z²³)

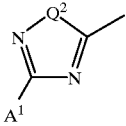 (Z²⁴)

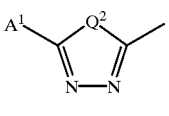 (Z²⁵)

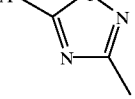 (Z²⁶)

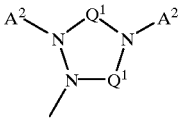 (Z²⁷)

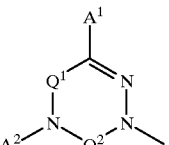 (Z²⁸)

where in each case $Q^1$ represents a group selected from the series —CO—, —CS—, —CH$_2$—, —CH(OH)—, —CHCl—, —CHBr—, —C(=CH$_2$)—, —C(=CHF)—, —C(=CF$_2$)—, —C(=CHCl)—, —C(=CHBr)—, —C(=CHOCHF$_2$)—, —C(=CHOCF$_3$)—, —C(=CHOCH$_2$CF$_3$)—, $Q^2$ represents oxygen, sulphur or a group selected from the series —CO—, —CS—, —CH$_2$—, —CHF—, —CF$_2$—, —CHCl—, CHBr—, —CHOCHF$_2$—, —CHOCF$_3$—, —CHOCH$_2$CF$_3$—, $A^1$ represents hydrogen, amino, nitro, cyano, carboxyl, carbamoyl, fluorine, chlorine, bromine, methyl, ethyl, n- or i-propyl, cyclopropyl, difluoromethyl, trifluoromethyl, chlorodifluoromethyl, methoxy, ethoxy, n- or i-propoxy, difluoromethoxy, trifluoromethoxy, chlorodifluoromethoxy, methylthio, ethylthio, n- or i-propylthio, difluoromethylthio, trifluoromethylthio, chlorodifluoromethylthio, methylamino, ethylamino, n- or i-propylamino, dimethylamino, diethylamino, methoxycarbonyl or ethoxycarbonyl, and $A^2$ represents hydrogen, hydroxyl, amino, cyano, methyl, ethyl, n- or i-propyl, difluoromethyl, methoxy, ethoxy, n- or i-propoxy, or where optionally two adjacent groups—$A^1$ and $A^1$ or $A^2$ and $A^2$ or $A^1$ and $A^2$—together represent alkanediyl or alkenediyl having in each case up to 4 carbon atoms and being in each case optionally substituted by fluorine, chlorine, bromine, methyl, ethyl, n- or i-propyl and being optionally interrupted by oxygen, sulphur or a group selected from the series —SO—, SO$_2$—, —N(CH$_3$)— or N(C$_2$H$_5$)— at the beginning (or at the end) or within the hydrocarbon chain.

Examples of the compounds of the formula (I) which can be prepared by the process according to the invention are listed in the groups below.

Group 1

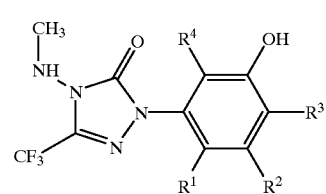

(IA-1)

| $R^1$ | $R^2$ | $R^3$ | $R^4$ |
|---|---|---|---|
| F | H | CN | H |
| Cl | H | CN | H |
| H | Cl | H | H |
| Cl | H | Cl | F |
| F | H | Cl | H |
| F | Cl | Cl | H |
| Cl | H | CF$_3$ | Cl |
| CH$_3$ | H | CF$_3$ | Cl |
| Br | H | CF$_3$ | Cl |
| CN | H | CF$_3$ | Cl |
| SC$_2$H$_5$ | H | CN | H |
| OCH$_3$ | H | CN | H |
| F | Cl | CN | H |
| F | H | CF$_3$ | Cl |
| Cl | H | NO$_2$ | H |
| Cl | H | NO$_2$ | Cl |
| CF$_3$ | H | NO$_2$ | H |
| NO$_2$ | H | CF$_3$ | H |
| H | Cl | CN | CH$_3$ |

Group 2

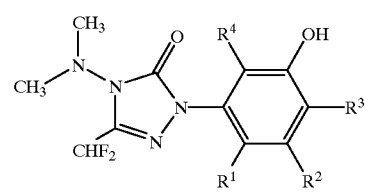

(IA-2)

In this context, $R^1$, $R^2$, $R^3$ and $R^4$ have, for example, the meanings given above in Group 1.

Group 3

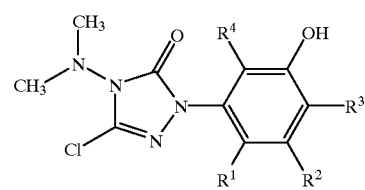

(IA-3)

In this context, $R^1$, $R^2$, $R^3$ and $R^4$ have, for example, the meanings given above in Group 1.

Group 4

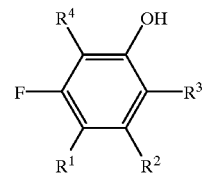

(IA-4)

In this context, $R^1$, $R^2$, $R^3$ and $R^4$ have, for example, the meanings given above in Group 1.

Group 5

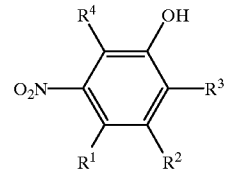

(IA-5)

In this context, $R^1$, $R^2$, $R^3$ and $R^4$ have, for example, the meanings given above in Group 1.

Group 6

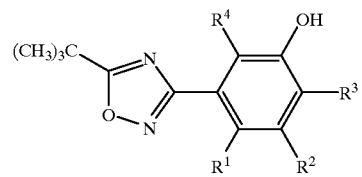

(IA-6)

In this context, $R^1$, $R^2$, $R^3$ and $R^4$ have, for example, the meanings given above in Group 1

Group 7

(IA-7)

In this context, $R^1$, $R^2$, $R^3$ and $R^4$ have, for example, the meanings given above in Group 1.

Group 8

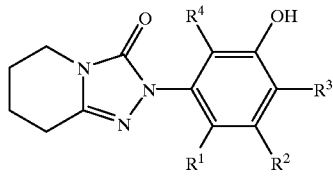
(IA-8)

In this context, $R^1$, $R^2$, $R^3$ and $R^4$ have, for example, the meanings given above in Group 1.

Group 9

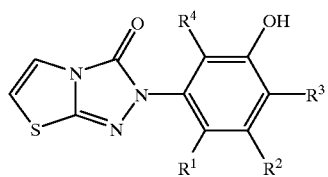
(IA-9)

In this context, $R^1$, $R^2$, $R^3$ and $R^4$ have, for example, the meanings given above in Group 1.

Group 10

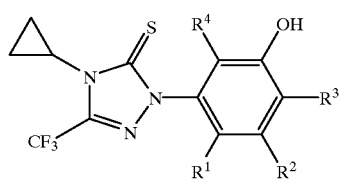
(IA-10)

In this context, $R^1$, $R^2$, $R^3$ and $R^4$ have, for example, the meanings given above in Group 1.

Group 11

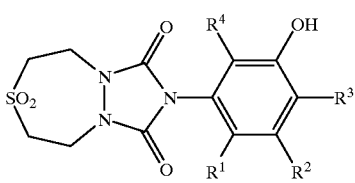
(IA-11)

In this context, $R^1$, $R^2$, $R^3$ and $R^4$ have, for example, the meanings given above in Group 1.

Group 12

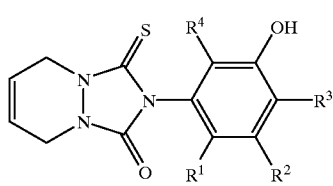
(IA-12)

In this context, $R^1$, $R^2$, $R^3$ and $R^4$ have, for example, the meanings given above in Group 1.

Group 13

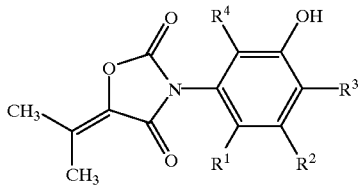
(IA-13)

In this context, $R^1$, $R^2$, $R^3$ and $R^4$ have, for example, the meanings given above in Group 1.

Group 14

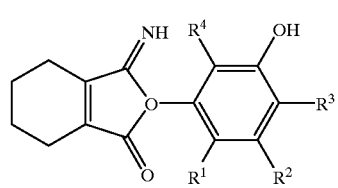
(IA-14)

In this context, $R^1$, $R^2$, $R^3$ and $R^4$ have, for example, the meanings given above in Group 1.

Group 15

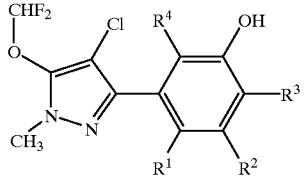
(IA-15)

In this context, $R^1$, $R^2$, $R^3$ and $R^4$ have, for example, the meanings given above in Group 1.

Group 16

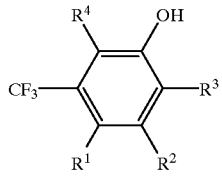
(IA-16)

In this context, $R^1$, $R^2$, $R^3$ and $R^4$ have, for example, the meanings given above in Group 1.

Group 17

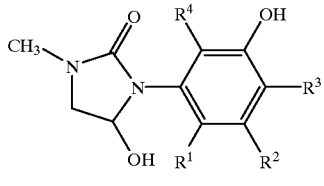
(IA-17)

In this context, $R^1$, $R^2$, $R^3$ and $R^4$ have, for example, the meanings given above in Group 1.

Group 18

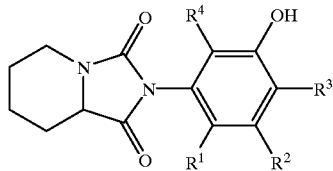
(IA-18)

In this context, $R^1$, $R^2$, $R^3$ and $R^4$ have, for example, the meanings given above in Group 1.

Group 19

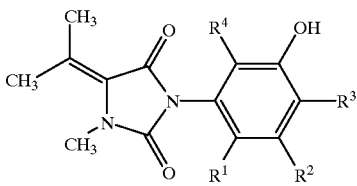
(IA-19)

In this context, $R^1$, $R^2$, $R^3$ and $R^4$ have, for example, the meanings given above in Group 1.

Group 20

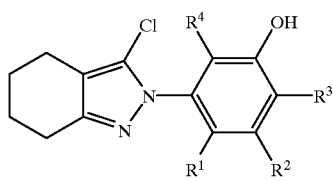
(IA-20)

In this context, $R^1$, $R^2$, $R^3$ and $R^4$ have, for example, the meanings given above in Group 1.

Group 21

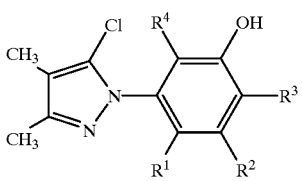
(IA-21)

In this context, $R^1$, $R^2$, $R^3$ and $R^4$ have, for example, the meanings given above in Group 1.

Group 22

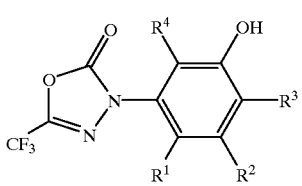
(IA-22)

In this context, $R^1$, $R^2$, $R^3$ and $R^4$ have, for example, the meanings given above in Group 1.

Group 23

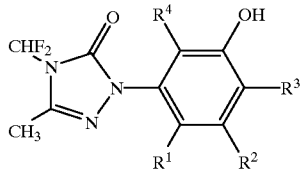
(IA-23)

In this context, $R^1$, $R^2$, $R^3$ and $R^4$ have, for example, the meanings given above in Group 1.

Group 24

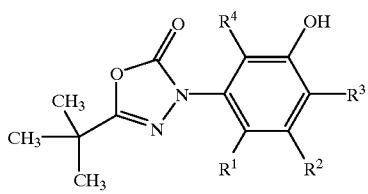
(IA-24)

In this context, $R^1$, $R^2$, $R^3$ and $R^4$ have, for example, the meanings given above in Group 1.

Group 25

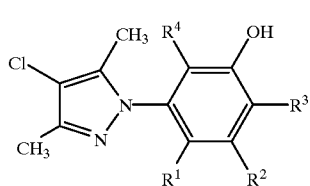
(IA-25)

In this context, $R^1$, $R^2$, $R^3$ and $R^4$ have, for example, the meanings given above in Group 1.

Group 26

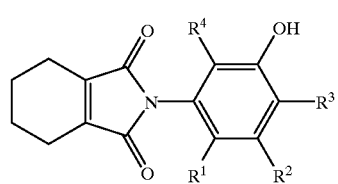
(IA-26)

In this context, $R^1$, $R^2$, $R^3$ and $R^4$ have, for example, the meanings given above in Group 1.

Group 27

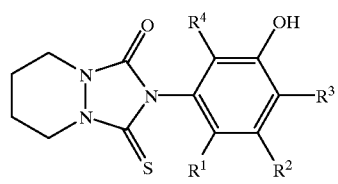
(IA-27)

In this context, $R^1$, $R^2$, $R^3$ and $R^4$ have, for example, the meanings given above in Group 1.

Group 28

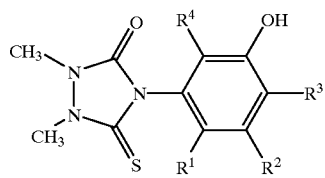
(IA-28)

In this context, $R^1$, $R^2$, $R^3$ and $R^4$ have, for example, the meanings given above in Group 1.

Group 29

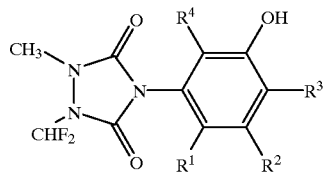
(IA-29)

In this context, $R^1$, $R^2$, $R^3$ and $R^4$ have, for example, the meanings given above in Group 1.

Group 30

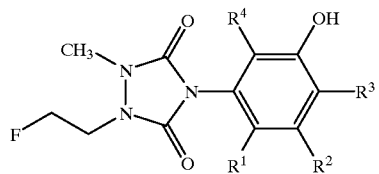
(IA-30)

In this context, $R^1$, $R^2$, $R^3$ and $R^4$ have, for example, the meanings given above in Group 1.

Group 31

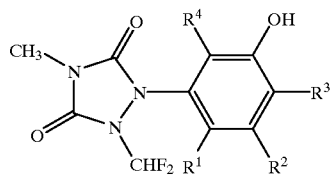
(IA-31)

In this context, $R^1$, $R^2$, $R^3$ and $R^4$ have, for example, the meanings given above in Group 1.

Group 32

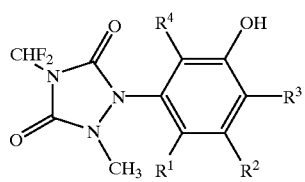
(IA-32)

In this context, $R^1$, $R^2$, $R^3$ and $R^4$ have, for example, the meanings given above in Group 1.

Group 33

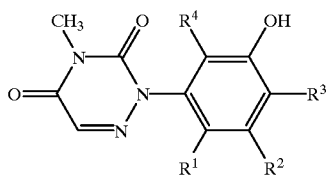
(IA-33)

In this context, $R^1$, $R^2$, $R^3$ and $R^4$ have, for example, the meanings given above in Group 1.

Group 34

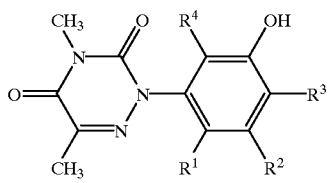
(IA-34)

In this context, $R^1$, $R^2$, $R^3$ and $R^4$ have, for example, the meanings given above in Group 1.

Group 35

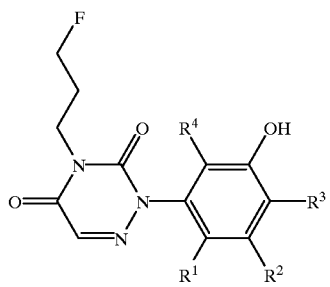
(IA-35)

In this context, $R^1$, $R^2$, $R^3$ and $R^4$ have, for example, the meanings given above in Group 1.

Group 36

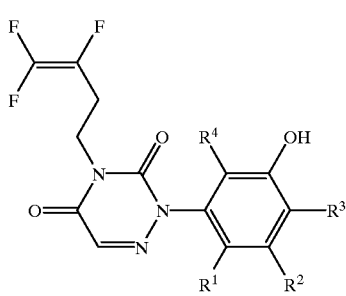
(IA-36)

In this context, $R^1$, $R^2$, $R^3$ and $R^4$ have, for example, the meanings given above in Group 1.

Group 37

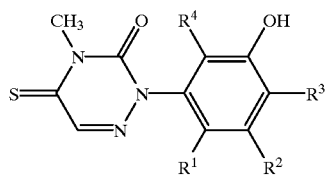
(IA-37)

In this context, $R^1$, $R^2$, $R^3$ and $R^4$ have, for example, the meanings given above in Group 1.

Group 38

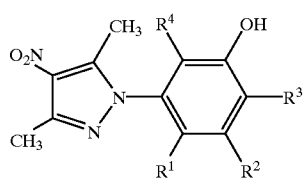
(IA-38)

In this context, $R^1$, $R^2$, $R^3$ and $R^4$ have, for example, the meanings given above in Group 1.

Group 39

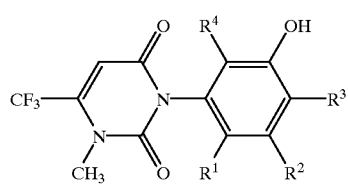
(IA-39)

In this context, $R^1$, $R^2$, $R^3$ and $R^4$ have, for example, the meanings given above in Group 1.

Group 40

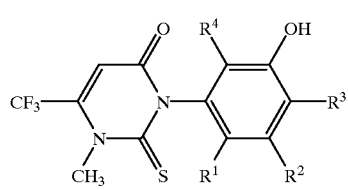
(IA-40)

In this context, $R^1$, $R^2$, $R^3$ and $R^4$ have, for example, the meanings given above in Group 1.

Group 41

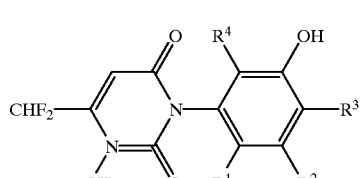
(IA-41)

In this context, $R^1$, $R^2$, $R^3$ and $R^4$ have, for example, the meanings given above in Group 1.

Group 42

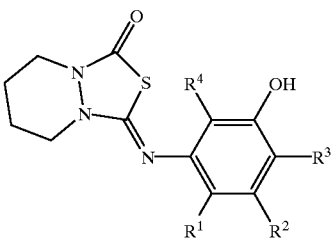
(IA-42)

In this context, $R^1$, $R^2$, $R^3$ and $R^4$ have, for example, the meanings given above in Group 1.

Group 43

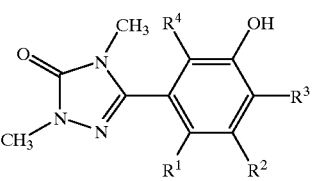
(IA-43)

In this context, $R^1$, $R^2$, $R^3$ and $R^4$ have, for example, the meanings given above in Group 1.

Group 44

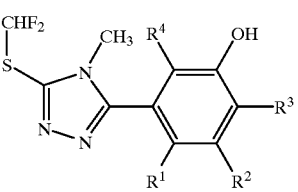
(IA-44)

In this context, $R^l$, $R^2$, $R^3$ and $R^4$ have, for example, the meanings given above in Group 1.

Group 45

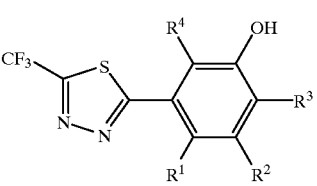
(IA-45)

In this context, $R^1$, $R^2$, $R^3$ and $R^4$ have, for example, the meanings given above in Group 1.

Group 46

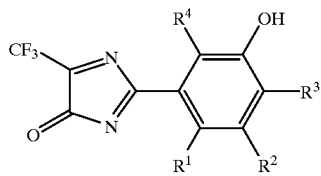
(IA-46)

In this context, $R^1$, $R^2$, $R^3$ and $R^4$ have, for example, the meanings given above in Group 1.

Group 47

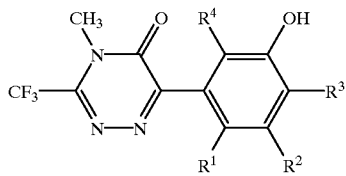
(IA-47)

In this context, $R^1$, $R^2$, $R^3$ and $R^4$ have, for example, the meanings given above in Group 1.

Group 48

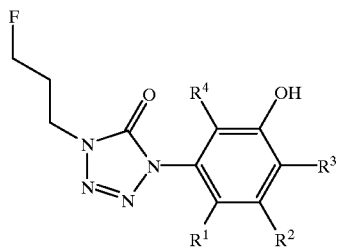
(IA-48)

In this context, $R^1$, $R^2$, $R^3$ and $R^4$ have, for example, the meanings given above in Group 1.

Group 49

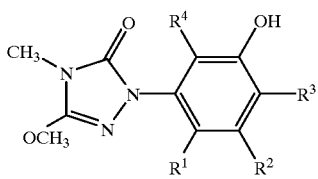
(IA-49)

In this context, $R^1$, $R^2$, $R^3$ and $R^4$ have, for example, the meanings given above in Group 1.

Group 50

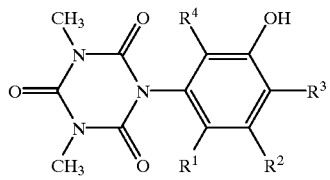
(IA-50)

In this context, $R^1$, $R^2$, $R^3$ and $R^4$ have, for example, the meanings given above in Group 1.

Group 51

(IA-51)

In this context, $R^1$, $R^2$, $R^3$ and $R^4$ have, for example, the meanings given above in Group 1.

Group 52

(IA-52)

In this context, $R^1$, $R^2$, $R^3$ and $R^4$ have, for example, the meanings given above in Group 1.

Group 53

(IA-53)

In this context, $R^1$, $R^2$, $R^3$ and $R^4$ have, for example, the meanings given above in Group 1.

Group 54

(IA-54)

In this context, $R^1$, $R^2$, $R^3$ and $R^4$ have, for example, the meanings given above in Group 1.

Group 55

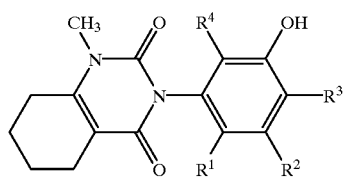
(IA-55)

In this context, $R^1$, $R^2$, $R^3$ and $R^4$ have, for example, the meanings given above in Group 1.

Group 56

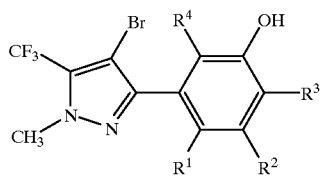
(IA-56)

In this context, $R^1$, $R^2$, $R^3$ and $R^4$ have, for example, the meanings given above in Group 1.

Group 57

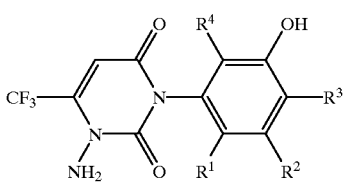
(IA-57)

In this context, $R^1$, $R^2$, $R^3$ and $R^4$ have, for example, the meanings given above in Group 1.

Group 58

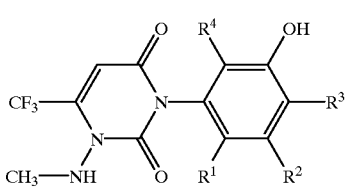
(IA-58)

In this context, $R^1$, $R^2$, $R^3$ and $R^4$ have, for example, the meanings given above in Group 1.

Group 59

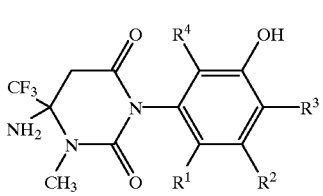
(IA-59)

In this context, $R^1$, $R^2$, $R^3$ and $R^4$ have, for example, the meanings given above in Group 1.

Group 60

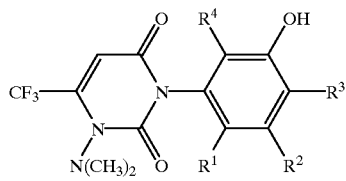
(IA-60)

In this context, $R^1$, $R^2$, $R^3$ and $R^4$ have, for example, the meanings given above in Group 1.

Group 61

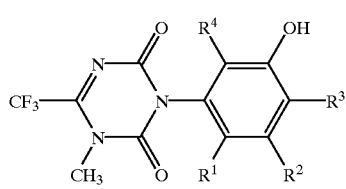
(IA-61)

In this context, $R^1$, $R^2$, $R^3$ and $R^4$ have, for example, the meanings given above in Group 1.

Group 62

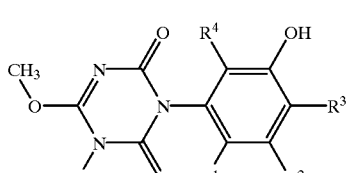
(IA-62)

In this context, $R^1$, $R^2$, $R^3$ and $R^4$ have, for example, the meanings given above in Group 1.

Group 63

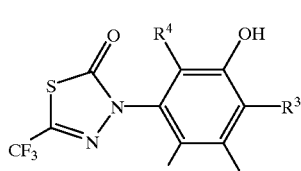
(IA-63)

In this context, $R^1$, $R^2$, $R^3$ and $R^4$ have, for example, the meanings given above in Group 1.

Group 64

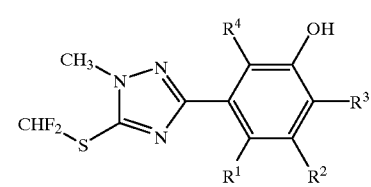
(IA-64)

In this context, $R^1$, $R^2$, $R^3$ and $R^4$ have, for example, the meanings given above in Group 1.

Group 65

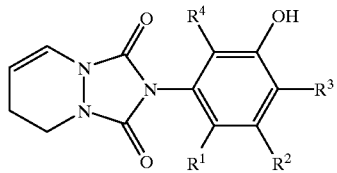
(IA-65)

In this context, $R^1$, $R^2$, $R^3$ and $R^4$ have, for example, the meanings given above in Group 1.

Group 66

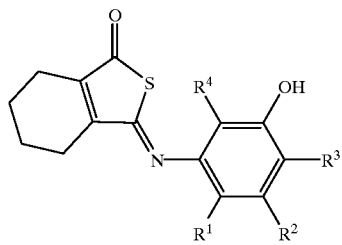
(IA-66)

In this context, $R^1$, $R^2$, $R^3$ and $R^4$ have, for example, the meanings given above in Group 1.

Group 67

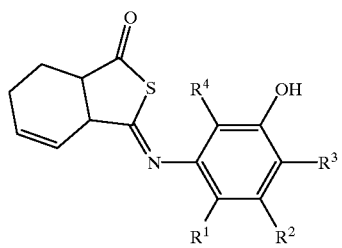
(IA-67)

In this context, $R^1$, $R^2$, $R^3$ and $R^4$ have, for example, the meanings given above in Group 1.

Group 68

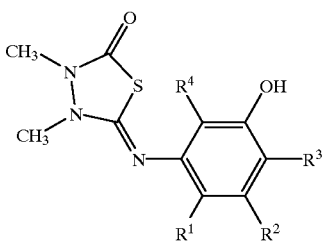
(IA-68)

In this context, $R^1$, $R^2$, $R^3$ and $R^4$ have, for example, the meanings given above in Group 1.

Group 69

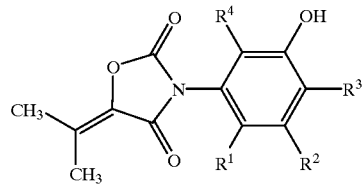
(IA-69)

In this context, $R^1$, $R^2$, $R^3$ and $R^4$ have, for example, the meanings given above in Group 1.

Group 70

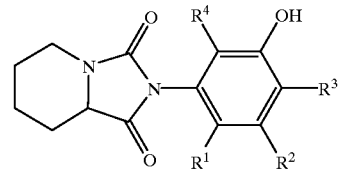
(IA-70)

In this context, $R^1$, $R^2$, $R^3$ and $R^4$ have, for example, the meanings given above in Group 1.

Group 71

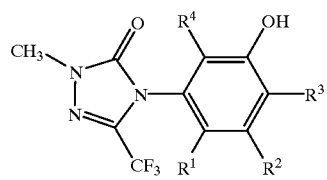
(IA-71)

In this context, $R^1$, $R^2$, $R^3$ and $R^4$ have, for example, the meanings given above in Group 1.

Using, for example, 2-fluoro-4-trifluoromethyl-benzonitrile and 3-hydroxy-propionitrile as starting materials, the course of the reaction in the process according to the invention can be illustrated by the following equation:

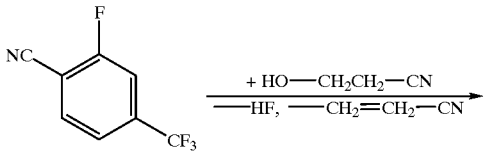

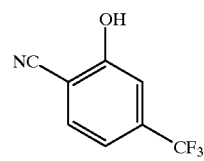

The formula (II) provides a general definition of the halogenoarenes to be used as starting materials in the process according to the invention for preparing compounds of the formula (I). In the formula (II), n, R and Z preferably or in particular have those meanings which have already been indicated above, in connection with the description of the compounds of the formula (I) according to the invention, as being preferred or as being particularly preferred for n, R and Z; X preferably represents fluorine, chlorine or bromine, in particular fluorine or chlorine.

The starting materials of the general formula (II) are known and/or can be prepared by known processes (cf. EP 609734, EP 648749, EP 648772).

The 3-hydroxy-propionitrile of the formula (III) further to be employed as starting material in the process according to the invention is a known chemical for synthesis.

The process according to the invention for preparing compounds of the general formula (I) is preferably carried out using a reaction auxiliary. Reaction auxiliaries which are suitable for this purpose are generally the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide, magnesium hydroxide, calcium hydroxide or barium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylaminopyridine, N-methyl-piperidine, 1,4-diazabicyclo[2,2,2]octane (DABCO), 1,5-diazabicyclo[4,3,0]-non-5-ene (DBN), or 1,8 diazabicyclo[5,4,0]-undec-7-ene (DBU).

Very particularly preferred reaction auxiliaries are alkali metal or alkaline earth metal hydrides, such as, for example, sodium hydride or calcium hydride, alkali metal or alkaline earth metal hydroxides, such as, for example, sodium hydroxide, potassium hydroxide, or calcium hydroxide, and also alkali metal alkoxides, such as, for example, sodium t-butoxide or potassium t-butoxide.

The process according to the invention for preparing compounds of the general formula (I) is preferably carried out using a diluent. Diluents which are suitable for this purpose are especially inert organic solvents. These include in particular aliphatic, alicyclic or aromatic, optionally halogenated hydrocarbons, such as, for example, benzine, paraffin, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, methyl t-butyl ether (MTBE), t-amyl methyl ether (TAME), dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides, such as dimethyl sulphoxide, or sulphones, such as tetramethylene-sulphone.

Diluents which are very particularly preferred are aprotic polar organic solvents, such as, for example, methyl t-butyl ether (MTBE), t-amyl methyl ether (TAME), methyl isobutyl ketone, acetonitrile, propionitrile or butyronitrile.

When carrying out the process according to the invention, the reaction temperatures can be varied within a relatively wide range. In general, the reaction is carried out at temperatures between 0° C. and 10° C., preferably between 10° C. and 60° C.

The process according to the invention is generally carried out under atmospheric pressure. However, it is also possible to carry out the process according to the invention under elevated or reduced pressure—in general between 0.1 bar and 10 bar.

When carrying out the process according to the invention, generally 1.0 to 5.0 mol, preferably 1.1 to 3.0 mol, of 3-hydroxy-propionitrile of the formula (III) and, if appropriate, 1.0 to 5.0 mol, preferably 1.1 to 3.0 mol, of reaction auxiliary are employed per mole of halogenoarene of the formula (II).

In a preferred embodiment of the process according to the invention, the 3-hydroxy-propionitrile of the formula (III) is initially charged in a suitable diluent, and the reaction auxiliary is then added. The mixture is briefly stirred at room temperature (approximately 20° C.), the halogenoarene of the formula (II) is added and the reaction mixture is stirred until the reaction has ended. Work-up and isolation of the reaction products is carried out by known methods (cf. the Preparation Examples).

The hydroxyarenes which can be prepared by the process according to the invention are biologically active compounds and/or can be employed as intermediates for preparing biologically active compounds, in particular herbicides (cf. EP 609734, EP 648749, EP 648772).

PREPARATION EXAMPLES

Example 1

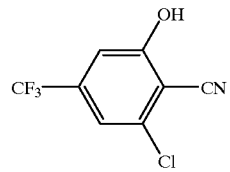

At 25° C., 0.99 g (33 mmol) of sodium hydride (80% strength in paraffin) are introduced a little at a time into a mixture of 2.3 g (33 mmol) of 3-hydroxy-propionitrile and 100 ml of acetonitrile. The mixture is stirred at room temperature (approximately 20° C.) for about 15 minutes and subsequently admixed with 7.2 g (30 mol) of 2,6-dichloro-4-trifluoromethyl-benzonitrile and stirred at room temperature for 12 hours. The mixture is concentrated under water pump vacuum, the residue is taken up in water and acidified using conc. hydrochloric acid and the precipitated product is isolated by filtration.

This gives 5.6 g (84% of theory) of 2-cyano-3-chloro-5-trifluoromethyl-phenol of melting point 138° C.

Example 2

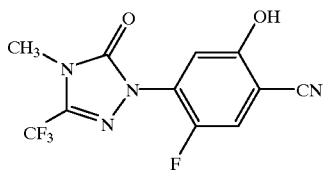

At approximately 20° C., 71 g (1.0 mol) of 3-hydroxy-propionitrile in 500 ml of acetonitrile are admixed a little at a time with 28.8 g (1.0 mol) of sodium hydride (80% strength in paraffin), and the mixture is then stirred at 25° C. for 15 minutes. 121.6 g (0.4 mol) of 2-(2.5-difluoro-4-cyano-phenyl)-4-methyl-5-trifluoromethyl-2,4-dihydro-3H-1,2,4-triazol-3-one are subsequently introduced, and the reaction mixture is stirred at approximately 25° C. for 12 hours. The mixture is then poured onto ice-water and acidified using conc. hydrochloric acid, and the precipitated product is isolated by filtration.

This gives 114 g (94% of theory) of 2-(2-fluoro-4-cyano-5-hydroxy-phenyl)-4-methyl-5-trifluoromethyl-2,4-dihydro-3H-1,2,4-triazol-3-one of melting point 208° C.

Example 3

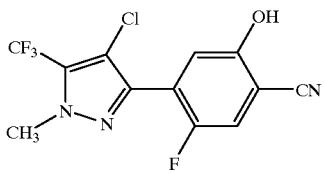

4.5 g (0.15 mol) of 80% strength sodium hydride in mineral oil are added to a solution of 11.0 g (0.15 mol) of 3-hydroxy-propionitrile in 100 ml of acetonitrile. The mixture is stirred at room temperature (approximately 20° C.) for about 15 minutes and then admixed with 19.3 g (0.06 mol) of 4-chloro-3-(4-cyano-2,5-difluoro-phenyl)-1-methyl-5-trifluoromethyl-1H-pyrazole. The reaction mixture is stirred at room temperature for 16 hours and then admixed with water and dichloromethane and acidified with hydrochloric acid, and the organic phase is separated off. The organic phase is washed successively with saturated sodium bicarbonate and sodium chloride solution, dried over magnesium sulphate and freed of the solvent using water pump vacuum. The crude product obtained in this manner is purified by column chromatography using dichloromethane as mobile phase.

This gives 6.1 g (32% of theory) of 4-chloro-3-(4-cyano-2-fluoro-5-hydroxy-phenyl)-1-methyl-5-trifluoromethyl-1H-pyrazole of melting point 151° C.

By the methods of Preparation Examples 1 to 3 and in accordance with the general description of the process according to the invention, it is also possible to prepare, for example, the compounds of the formula (IB) below listed in Table 1.

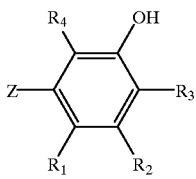

(IB)

TABLE 1

Examples of compounds of the formula (IB) preparable according to the invention

| Ex. No. | $R^1$ | $R^2$ | $R^3$ | $R^4$ | Z | Melting point (° C.) |
|---|---|---|---|---|---|---|
| 4 | CN | F | H | H | F | 169 |
| 5 | F | H | CN | H | CN | 198 |
| 6 | F | H | CN | H | (triazolone with CH₃, CHF₂) | 157 |
| 7 | CN | H | F | Cl | F | 129 |
| 8 | F | H | CN | H | (triazolone with C₂H₅, CF₃) | 200 |
| 9 | CN | H | Cl | H | Cl | 194 |
| 10 | F | H | CN | H | (pyrazole with OCHF₂, Br, CH₃) | 129 |
| 11 | CN | Cl | H | H | Cl | 180 |
| 12 | F | H | CN | H | (pyrimidinedione with F₃C, methyl) | ¹H-NMR (DMSO-D₆): 6.39 (s. 1H) δ, ppm |

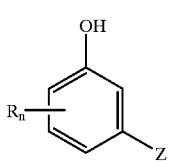

What is claimed is:
1. Process for preparing hydroxyarenes of the general formula (I)

(I)

in which
n represents the numbers 1, 2, 3 or 4,

R represents cyano, carboxyl, formyl, nitro, halogen or represents alkyl, alkoxy, alkylthio, alkylsulphinyl, alkylsulphonyl, alkylcarbonyl or alkoxycarbonyl, each of which is optionally substituted, and Z represents hydrogen, cyano, nitro, halogen, alkyl, halogenoalkyl, or represents monocyclic or bicyclic, saturated or unsaturated heterocyclyl, heterocyclylamino or heterocyclylimino, each of which is optionally substituted, characterized in that
halogenoarenes of the general formula (II)

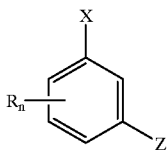

in which
n, R and Z are each as defined above and
X represents halogen
are reacted with 3-hydroxy-propionitrile of the formula (III)

HO—CH$_2$CH$_2$—CN          (III).

2. Process according to claim 1, characterized in that halogenoarenes of the formula (II) are used in which n represents the numbers 1, 2 or 3, R represents cyano, carboxyl, formyl, nitro, halogen or represents alkyl, alkoxy, alkylthio, alkylsulphinyl, alkylsulphonyl, alkylcarbonyl or alkoxycarbonyl having in each case 1 to 6 carbon atoms and being in each case optionally substituted by cyano, halogen, $C_1$–$C_4$-alkoxy or $C_1$–$C_4$-alkylthio, Z represents hydrogen, cyano, halogen or represents monocyclic or bicyclic, saturated or unsaturated heterocyclyl, heterocyclylamino or heterocyclylimino having in each case 2 to 6 carbon atoms and 1 to 4 nitrogen atoms in the heterocyclic ring system and being in each case optionally substituted, which optionally additionally contains an oxygen or sulphur atom and/or optionally up to three groups selected from the series —CO—, —CS—, —SO— and/or SO$_2$—, and which is optionally substituted by one or more groups selected from the series nitro, hydroxyl, amino, cyano, carboxyl, carbamoyl, thiocarbamoyl halogen, $C_1$–$C_6$-alkyl which is optionally substituted by halogen or $C_1$–$C_4$-alkoxy, $C_2$–$C_6$-alkenyl or $C_3$–$C_6$-alkinyl which are in each case optionally substituted by halogen, $C_1$–$C_6$-alkoxy or $C_1$–$C_6$-alkoxy-carbonyl which are in each case optionally substituted by halogen or $C_1$–$C_4$-alkoxy, $C_2$–$C_6$-alkenyloxy or $C_2$–$C_6$-alkinyloxy which are in each case optionally substituted by halogen, $C_1$–$C_6$-alkylthio, $C_2$–$C_6$-alkenylthio or $C_2$–$C_6$-alkinylthio which are in each case optionally substituted by halogen, $C_1$–$C_6$-alkylamino or di-($C_1$–$C_4$-alkyl)-amino, $C_3$–$C_6$-cycloalkyl or $C_3$–$C_6$cycloalkyl-$C_1$–$C_4$-alkyl (which are in each case optionally substituted by halogen and/or $C_1$–$C_4$-alkyl), phenyl, phenoxy, phenylthio, phenylsulphinyl, phenylsulphonyl or phenylamino which are in each case optionally substituted by nitro, cyano, halogen, $C_1$–$C_4$-alkyl, $C_1$–$C_4$-halogenoalkyl, $C_1$–$C_4$-alkyloxy, $C_1$–$C_4$-halogenoalkyloxy and/or $C_1$–$C_4$-alkoxy-carbonyl, and X represents fluorine, chlorine or bromine.

3. Process according to claim 1, characterized in that halogenoarenes of the formula (II) are used in which n represents the numbers 1 or 2, R represents cyano, carboxyl, formyl, nitro, halogen or represents methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl or ethoxycarbonyl, each of which is optionally substituted by cyano, halogen, methoxy, ethoxy, methylthio or ethylthio, Z represents hydrogen, cyano, halogen or represents monocyclic or bicyclic, saturated or unsaturated heterocycly, heterocyclylamino or heterocyclylimino having in each case 2 to 6 carbon atoms and 1 to 4 nitrogen atoms in the heterocyclic ring system and being in each case optionally substituted, which optionally additionally contains an oxygen or sulphur atom and/or optionally up to two groups selected from the series —CO—, —CS—, —SO— and/or SO$_2$—, and which is optionally substituted by one or more groups selected from the series nitro, hydroxyl, amino, cyano, carboxyl, carbamoyl, thiocarbamoyl, fluorine, chlorine, bromine; methyl, ethyl, n- or i-propyl, n-, i-, s- or t-butyl which are optionally substituted by fluorine, chlorine, methoxy or ethoxy; propenyl, butenyl, propinyl or butinyl (which are in each case optionally substituted by fluorine or chlorine); methoxy, ethoxy, n- or i-propoxy, n-, i-, s- or t-butoxy, methoxycarbonyl or ethoxycarbonyl which are in each case optionally substituted by fluorine, chlorine, methoxy or ethoxy); propenyloxy, butenyloxy, propinyloxy or butinyloxy which are optionally substituted by fluorine or chlorine; methylthio, ethylthio, n- or i-propylthio, n-, i-, s- or t-butylthio, propenylthio, butenylthio, propinylthio or butinylthio which are in each case optionally substituted by fluorine or chlorine; methylamino, ethylamino, n- or i-propylamino, n-, i-, s- or t-butylamino, dimethylamino or diethylamino; cyclopropyl, cyclobutyl, cyclopentyl, cyclohexyl, cyclopropylmethyl, cyclobutylmethyl, cyclopentylmethyl or cyclohexylmethyl which are in each case optionally substituted by fluorine, chlorine, methyl, ethyl, n- or i-propyl, phenyl, phenoxy, phenylthio, phenylsulphinyl, phenylsulphonyl or phenylamino which are in each case optionally substituted by nitro, cyano, fluorine, chlorine, bromine, methyl, ethyl, n- or i-propyl, trifluoromethyl, methoxy, ethoxy, n- or i-propoxy, difluoromethoxy, trifluoromethoxy, methoxycarbonyl or ethoxycarbonyl; and X represents fluorine or chlorine.

4. Process according to claim 1, characterized in that this process is carried out in the presence of a reaction auxiliary.

5. Process according to claim 1, characterized in that this process is carried out in the presence of a diluent.

6. Process according to claim 1, characterized in that this process is carried out at temperatures between 0 and 100° C.

7. Process according to claim 2, characterized in that this process is carried out in the presence of a reaction auxiliary, in the presence of a diluent, and at temperatures between 0 and 100° C.

8. Process according to claim 3, characterized in that this process is carried out in the presence of a reaction auxiliary, in the presence of a diluent, and at temperatures between 0 and 100° C.

* * * * *